United States Patent [19]

Weinkauf et al.

[11] 4,134,018
[45] Jan. 9, 1979

[54] TOMOGRAPHIC APPARATUS FOR PRODUCING TRANSVERSE LAYER IMAGES

[75] Inventors: Burghard Weinkauf, Erlangen; Günter Luderer, Eltersdorf, both of Germany

[73] Assignee: Siemens Aktiengesellschaft, Berlin & Munich, Germany

[21] Appl. No.: 809,806

[22] Filed: Jun. 24, 1977

[30] Foreign Application Priority Data

Jul. 6, 1976 [DE] Fed. Rep. of Germany ....... 2630399

[51] Int. Cl.$^2$ .............................................. A61B 6/02
[52] U.S. Cl. .............................. 250/445 T; 250/363 S; 250/385
[58] Field of Search ................ 250/445 T, 360, 363 S, 250/385, 386

[56] References Cited

U.S. PATENT DOCUMENTS 4,068,306   1/1978   Chen et al. ........................ 250/445 T Primary Examiner—Alfred E. Smith
Assistant Examiner—T. N. Grigsby
Attorney, Agent, or Firm—Hill, Gross, Simpson, Van Santen, Steadman, Chiara & Simpson

[57] ABSTRACT

In an illustrated embodiment radiation detectors are associated with respective signal processing channels which have components subject to errors which vary in the course of time because of external influences such as temperature and aging effects. Each signal channel is subjected to a calibration cycle by introducing an impulse change in the supply voltage common to the respective detectors. Where xenon detectors are utilized in conjunction with integrators, the variation in detector gas volume and capacitance due to manufacturing tolerances may be compensated by storage of a constant value. Thereafter, calibration cycles may provide for automatic correction of the measurement signals for subsequent errors. A calibrating cycle can take place prior to initiation of a patient radiograph, or between two x-ray flashes during the angular scanning process.

3 Claims, 5 Drawing Figures

TOMOGRAPHIC APPARATUS FOR PRODUCING TRANSVERSE LAYER IMAGES

BACKGROUND OF THE INVENTION

The invention relates to a tomographic apparatus for producing transverse layer images of a radiographic subject with a radiation measuring arrangement comprising a radiation source which produces a fan-shaped radiation beam penetrating the radiographic subject, the extent of which beam in the layer plane is of such dimensions that the entire radiographic subject is penetrated, and also comprising a radiation receiver which determines the intensity of radiation behind the subject by scanning the projected radiation beam, and having also a driving mechanism for the measuring arrangement to effect rotational movements of the radiation measuring arrangement, and a measured value converter to transform the signals supplied by the radiation receiver into a layer image wherein the radiation receiver consists of a row of detectors, the detectors of which being connected by one pole to a common voltage supply device and the number of detectors being selected according to the desired image resolution.

It is known to use as detectors xenon-detectors lying at high voltage in the measured value converter as ionization chambers. Thus, all the image elements of the angular position, per angular position of the measuring arrangement, are measured simultaneously by way of a corresponding number of individual X-ray detectors, and the signals of the detectors are subsequently processed in parallel in separate measuring channels. Various types of errors occur with such a measuring arrangement. One cause of error resides in the differing sensitivities of the X-ray detectors due to their manufacturing tolerances. These errors do not change in the course of the operation. It is therefore sufficient to detect these errors once. There are, however, other errors which vary in the course of time, i.e., the differences in amplification of the measuring channels coordinated to the individual detectors of the measured value converter. These differences in amplification emanate, on the one hand, from structural element tolerances, but also, on the other hand, from external influences, e.g., temperature and aging influences.

SUMMARY OF THE INVENTION

The object underlying the invention is to create a tomographic X-ray apparatus of the type specified at the outset wherein it is possible to eliminate the described errors.

According to the invention this object is solved in that, in order to calibrate the structural elements contained in the signal processing channels of the detectors, there are provided means for a short-term change in the voltage lying at the pole common to all the detectors. In the tomographic X-ray apparatus according to the invention, a calibration of the signal processing channels is made possible in a particularly simple manner by means of a simple pulse-wise changing of the common supply voltage for the detectors. The described errors can thus be determined and taken into account.

A further specific object of the invention is to provide an automatic error compensation for the time-dependent errors in the respective signal processing channels of the measured value converter, such that multiplicative errors are essentially compensated as often as necessary. In a preferred implementation, a first memory is associated with each channel for storing a constant value for compensating for time-independent errors, and a second memory is provided for coupling with the output of the integrator for the respective channel, the detector of such channel receiving a high voltage pulse so as to enable such memory to sense time-dependent variations in the characteristics of the individual channel and to compensate the output of such channel for both such types of error.

Other objects, features and advantages of the invention will be apparent from the following detailed description taken in connection with the accompanying sheets of drawings.

DETAILED DESCRIPTION

Figure 1:
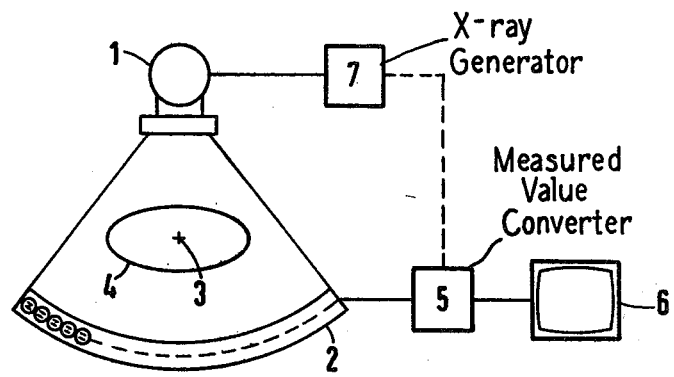
FIG. 1 shows schematically a known tomographic apparatus.

FIG. 1 shows schematically a known tomographic apparatus of this kind. It comprises an X-ray tube 1 and a radiation receiver 2 which has, according to size, over 100, e.g. 256, individual detectors arranged in a row. The radiation receiver 2 is curved about the focus of the X-ray tube 1. The measuring arrangement 1, 2 is adapted to be rotated about a point 3 which lies in the radiographic subject 4. The number of detectors of the radiation receiver 2 is selected according to the desired image resolution such that, following a rotation of the measuring arrangement 1, 2, an image can be calculated by a measured value converter 5. The image is reproduced on a video apparatus 6. On rotation of the measuring arrangement 1, 2, the X-ray tube 1 is switched on (pulsated) at specific angular positions, e.g. at each angular degree; that is, switched on for such a short time that the blurring resulting from the rotation is kept sufficiently slight. For this purpose, the X-ray generator 7 for the X-ray tube 1 is switched on to pulsate the X-ray tube 1. The measured values of the radiation receiver 2 occur synchronously with this. This is indicated by a broken line in FIG. 1.

It is known to use as detectors xenon-detectors lying at high voltage in the measured value converter as ionization chambers. Thus, all the image elements of the angular position, per angular position of the measuring arrangement 1, 2, are measured simultaneously by way of a corresponding number of individual X-ray detectors, and the signals of the detectors are subsequently processed in parallel in separate measuring channels. Various types of errors occur with such a measuring arrangement. One cause of error resides in the differing sensitivities of the X-ray detectors due to their manufacturing tolerances. These errors do not change in the course of the operation. It is therefore sufficient to detect these errors once. There are, however, other errors which vary in the course of time, i.e., the differences in amplification of the measuring channels coordinated to the individual detectors of the measured value converter. These differences in amplification emanate, on the one hand, from structural element tolerances, but also, on the other hand, from external influences, e.g., temperature and aging influences.

Figure 2:
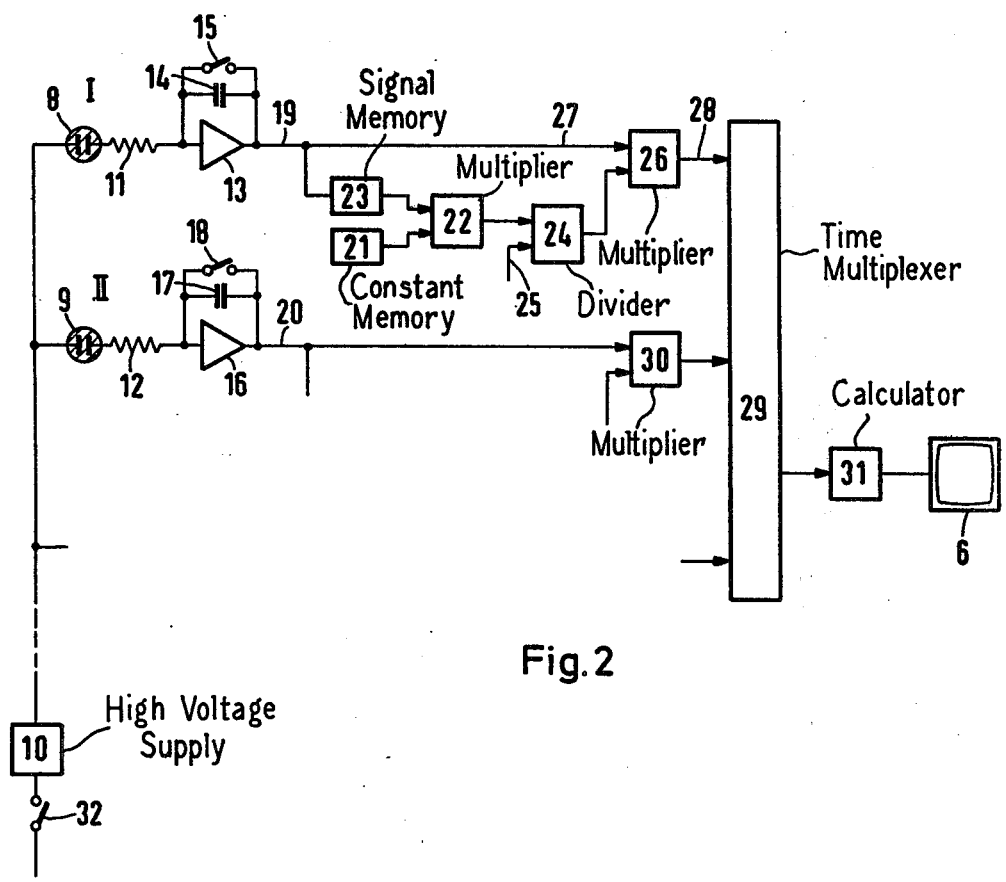
FIG. 2 shows a circuit diagram of the parts of the tomographic apparatus in accordance with the invention which are essential for an understanding of the invention.

FIG. 2 shows two xenon-detectors 8 and 9 from the set making up the radiation receiver 2. As already explained, more of these xenon-detectors are provided; more particularly, a number corresponding to the desired image resolution. The individual channels of the xenon-detectors are, however, constructed alike so that the invention will be described with reference to two channels only. All the xenon-detectors lie with one pole connected to a high voltage supply device 10 and with the other pole connected to an integrator via a current limiting resistance, of which current limiting resistances 11 and 12 are illustrated in FIG. 2. The integrator of channel I contains an amplifier 13, an integration capacitor 14, and a quenching switch 15, and the integrator of the channel II contains an amplifier 16, an integration capacitor 17, and a quenching switch 18.

Figure 3:
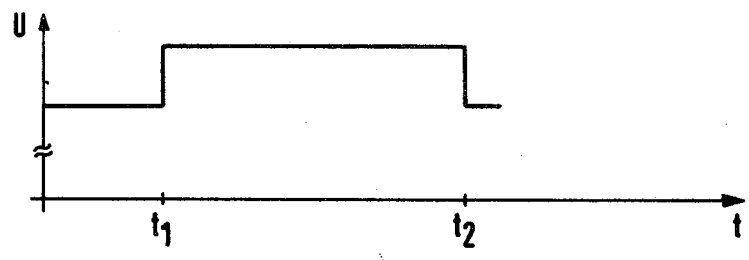
FIGS. 3, 4 and 5 show a wave form diagrams for explaining the operation of FIG. 2 during automatic calibration.
Figure 4:
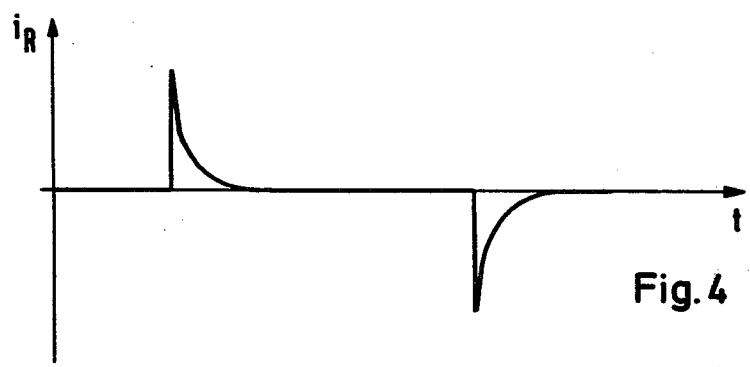
Figure 5:
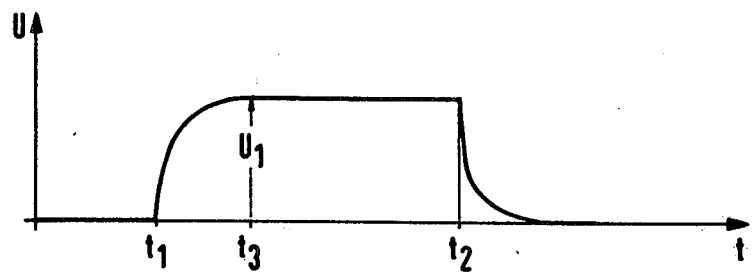

Through the invention, differences in sensitivity of the radiation detectors 8, 9, etc., arising from manufacturing tolerances, on the one hand, and tolerances of the structural elements of the channels, e.g., of the structural elements 11, 13, 14 and 12, 16, 17, respectively, which tolerances are a factor in the amplification, on the other hand, should now be determined and compensated. For this purpose, according to FIG. 3, the high voltage at the detectors 8, 9, etc., is increased for a short time; namely between the points of time $t_1$ and $t_2$. It is presupposed that no x-radiation is present, so that the content of the integration capacitors 14 and 17 is zero. As a result of the calibration pulse in accordance with FIG. 3, a current in accordance with FIG. 4 flows through the resistance 11 or 12, respectively. After the end of a calibration pulse in accordance with FIG. 3, the content of the integration capacitors 14 or 17 and thus the voltage at the channel output (point 19 or 20) again becomes zero. Between the points of time $t_1$ and $t_2$, according to FIG. 5, the signal voltage assumes a maximum value, however, which, in the example according to FIG. 5, is achieved at the point of time $t_3$. This voltage value $U_1$ can now be used, in the manner described hereinafter, to determine a calibration signal. It is important that the interrogation is effected at a suitable point of time between $t_3$ and $t_2$.

The detectors 8, 9, etc., are xenon-detectors which show sample scatterings which are the cause of displacement currents of differing magnitudes. The gas volume also differs in magnitude from detector to detector due to mechanical tolerances. However, there is no relationship between the capacity and the gas volume of a detector. Accordingly, for calibration purposes, two different measurements in immediate succession are first required prior to putting the tomographic X-ray apparatus into operation. First a measurement is taken with an X-ray calibration pulse which produces a signal proportional to the detector volume. A second measurement follows immediately thereafter with a voltage pulse at the high voltage of detector operation, which supplies a signal proportional to the detector capacity. This measurement therefore need be effected once only, expediently by the manufacturer of the apparatus, since the change in gas volume and capacity of a detector over a period of time is negligible. The quotient of the two signals at the channel outputs 19, 20, i.e., of one signal at the channel output which is produced by an X-ray calibration pulse, and one signal at the channel output which is produced by a high voltage pulse, results in a constant K, specific to the detector, which is determined in this manner once for each detector and stored. For storage, each channel contains a constant memory. In FIG. 2, this is only illustrated for the channel 1 where the constant memory is designated by reference numeral 21. The components 21–24 are provided for each channel, but in FIG. 2 are only illustrated for channel I. Thus, in the constant memory 21, there is stored a constant which is specific to the detector 8 and is manually fed (or put) in, for example, in the factory. With this stored constant, and with the signal at the channel output 19, which can be produced as often as desired between the times $t_1$ and $t_2$ by way of voltage pulses in accordance with FIG. 3, a calibration signal can be calculated. For this calibration signal E, the equation $E = K \cdot U_2$ is valid. $U_2$ is the signal voltage at the output 19 which appears as a result of a voltage pulse at the high voltage of detector operation (FIG. 3) at the moment of calibration. The calibration signal E is newly determined as often as required, e.g. daily before each patient radiograph or during the radiograph prior to a pulsation of the X-ray tube 1. $U_2$ is dependent on all the parameters which produce a multiplicative error, e.g., changes in amplification in the measuring channel caused by aging and temperature.

The calibration signal E is formed according to FIG. 2 in a multiplier 22 to which the constant K is supplied by the constant memory 21, and the voltage $U_2$ is supplied by a signal memory 23 for the voltage $U_2$ at the output 19. Thus, the calibration signal lies at the output of the multiplier 22. This calibration signal is compared in a divider 24 with a reference signal, lying at an input 25, which is the same for all channels; i.e. the divider 24 forms a quotient from the reference signal and the calibration signal and thus forms a calibration factor. A signal corresponding to the calibration factor lies at the output of the divider 24 and is supplied to a multiplier 26 in which it is multiplied with the measurement signal lying at the input 27 in the case of an X-ray pulse. In this way, the output signal of the multiplier 26 is free of the described errors at the output 28.

FIG. 2 shows a time multiplexer 29 which successively interrogates the outputs of the multipliers 26, 30, etc. of the individual channels and supplies the corresponding signals to a calculator 31 which calculates the cross-sectional image and effects its reproduction on the video apparatus 6. The structural elements 11 to 31 are thus a component part of the measured value converter 5.

The task of the quenching switches 15, 18, etc. is to quench the integrators 13, 14; 16, 17, when their signals have been processed, and they are consequently controlled by the calculator 31.

For the purpose of calibration of the channels, it is within the scope of the invention to render possible not only an impulse-wise increase in the operational voltage of the detectors 8, 9, etc., but to also render possible another impulse-wise change in this operational voltage, particularly a reduction. The pulse shape need not be rectangular but may also be sinusoidal, for example.

The calibration process in accordance with the invention does not require any X-ray calibration shots (or charges). Calibration is effected only with voltage pulses at the operational high voltage of the X-ray detectors 8, 9, etc. It may thus be effected fully automatically and as often as desired even during a current patient examination. The calibration extends to all the detectors as well as to the following electronic measuring apparatus of the channels. It may, of course, be effected in the described manner by way of a voltage pulse at the operational voltage only when no X-ray pulse is present. The structural elements 21 to 26 ensure an automatic correction of the measurement signals which are effected by multiplicative errors.

A switch 32 is illustrated schematically in FIG. 2 for the pulse-wise change in the common supply voltage for the detectors 8, 9, etc. This switch 32 can be closed automatically between the points of time $t_1$ and $t_2$ (FIGS. 3 to 5); for example, prior to initiation of a patient radiograph or between two X-ray flashes.

Constant memory 21 could be, for example, a potentiometer supplying a voltage according to constant K. Signal memory 23 would then be a sample and hold circuit such as found in electronic analog computers.

It will be apparent that many modifcations and variations may be effected without departing from the scope of the novel concepts and teachings of the present invention.

We claim as our invention:

1. A tomographic device for producing transverse layer images of a radiographic subject with a radiation measuring arrangement comprising a radiation source which produces a radiation beam penetrating the radiographic subject, the extent of which beam in the layer plane is of such dimensions that the entire radiographic subject is penetrated, and also comprising a radiation receiver which determines the intensity of radiation behind the subject by scanning the projected radiation beam, and with rotational movements of the radiation measuring arrangement, and comprising a measured value converter for transforming the signals supplied by the radiation receiver into a layer image, wherein the radiation receiver comprises a row of detectors, the detectors of which having one pole for connection to a common voltage supply, and the number of detectors being selected according to the desired image resolution, and signal processing channels (I, II, etc.,) connected to the respective detectors (8, 9, etc.), means (32) being provided for a short-term change in the voltage connected to the common pole of all the detectors for the calibration (8, 9, etc.), of such signal processing channels.

2. A tomographic device according to claim 1, characterized in that the detectors (8, 9 etc.) are ionization chambers, one of the poles of which being connected to a high voltage source (10), and that means (32) are provided for a pulse-wise change in the high voltage supplied to said one poles.

3. A tomographic device according to claim 1, characterized in that each channel (e.g. I) has a memory (21) for a constant typical of the channel, and a memory (23) for the calibration voltage tapped at an integrator (13, 14) for the detector voltage, that the output voltages of these two memories (21, 23) are connected to a multiplier (22), the output signal of which is supplied to a divider (24) which divides a reference signal by this output signal, and that the output of the divider (24) is connected to one input of a multiplier (26), to the other input (27) of which the measuring signal supplied by the integrator (13, 14) is supplied and whose output signal is processed in a calculator.

* * * * *